(12) United States Patent
Hall et al.

(10) Patent No.: US 8,727,986 B2
(45) Date of Patent: May 20, 2014

(54) METHOD AND APPARATUS FOR ASSESSING RISK OF PRETERM DELIVERY

(75) Inventors: Timothy Jon Hall, Madison, WI (US); Helen Marcie Feltovich, Minneapolis, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 573 days.

(21) Appl. No.: 12/395,018

(22) Filed: Feb. 27, 2009

(65) Prior Publication Data

US 2010/0222679 A1  Sep. 2, 2010

(51) Int. Cl.
*A61B 8/00* (2006.01)

(52) U.S. Cl.
USPC .......................................... 600/438; 600/462

(58) Field of Classification Search
USPC ......... 600/437, 438, 440, 441, 442, 443, 444, 600/445, 446, 447, 448, 449, 458, 459, 462, 600/463, 472, 587, 588, 372, 373, 591
See application file for complete search history.

(56) References Cited

U.S. PATENT DOCUMENTS

| 5,876,345 | A * | 3/1999 | Eaton et al. | 600/466 |
|---|---|---|---|---|
| 6,045,508 | A * | 4/2000 | Hossack et al. | 600/447 |
| 2004/0106869 | A1* | 6/2004 | Tepper | 600/443 |
| 2004/0210136 | A1* | 10/2004 | Varghese et al. | 600/443 |
| 2005/0234340 | A1* | 10/2005 | Brock-Fisher et al. | 600/458 |
| 2007/0083120 | A1* | 4/2007 | Cain et al. | 600/439 |
| 2007/0167755 | A1* | 7/2007 | Kolios et al. | 600/437 |
| 2007/0233191 | A1* | 10/2007 | Parmer | 607/1 |
| 2008/0269604 | A1* | 10/2008 | Boctor et al. | 600/437 |

OTHER PUBLICATIONS

McFarlin BL, O'Brien WD, Zachary JF, "Quantitative Ultrasound Assessment of the Rat Cervix" 2006, Journal of Ultrasound Medicine, vol. 25, p. 1031-1040, American Institute of Ultrasound in Medicine, Laurel, Maryland, USA.*
Chandra S, Crane JMG, Hutchens D, and Young DC. "Transvaginal Ultrasound and Digital Examination in Predicting Successful Labor Induction" Obstetrics & Gynecology: Jul. 2001—vol. 98—Issue 1—p. 2-6.*
McFarlin, Barbara L., et al., Quantitative Ultrasound Assessment of the Rat Cervix, Journal of Ultrasound Medicine 2006; vol. 25, pp. 1031-1040, American Institute of Ultrasound in Medicine, Laurel, Maryland, USA.

* cited by examiner

*Primary Examiner* — Unsu Jung
*Assistant Examiner* — Michael N Fisher
(74) *Attorney, Agent, or Firm* — Boyle Fredrickson, S.C.

(57) ABSTRACT

An apparatus for assessing the risk of preterm delivery and the success of induction of labor at term uses a steered ultrasound beam to assess microstructure of the cervix revealed by backscatter power attenuation at a range of angles. It is believed that objective and precise description of cervical microstructure will reveal stage of cervical remodeling an as such may reveal risk of preterm delivery and/or success of labor induction. The backscatter power loss can be combined with elasticity measurements to provide a more precise indication of tissue structure.

19 Claims, 6 Drawing Sheets

METHOD AND APPARATUS FOR ASSESSING RISK OF PRETERM DELIVERY

STATEMENT REGARDING FEDERALLY SPONSORED RESEARCH

- - -

CROSS-REFERENCE TO RELATED APPLICATIONS

- - -

BACKGROUND OF THE INVENTION

The present invention relates generally to ultrasonic equipment and in particular to an ultrasound machine and method of operating the ultrasound machine to assess cervical structure for the purpose of monitoring a pregnancy.

Abnormal cervical behavior contributes to both post-term and preterm pregnancy. With respect to the former, failed inductions of labor cause an increase in cesarean delivery, with longer hospitalizations and greater maternal/neonatal morbidity. Ultrasound prediction (measuring cervical length) and biochemical testing of cervical secretions do not effectively predict which patients at term will have successful inductions.

Preterm delivery is an even greater problem, resulting in significant infant mortality and morbidity (including long-term neurodisability) costing more than $26 billion annually in the US alone. Despite intense research, preterm birth rates have increased over the past century in part due to a lack of effective therapies in the face of a greater number of high-risk pregnancies. Drugs that reduce inflammation and/or inhibit uterine contractions do not prevent preterm birth, nor does cerclage (a suture around the cervix to tie it closed). Currently, ultrasound is used to measure cervical length in an effort to predict preterm delivery (associated with shortening). However, the American College of Obstetricians and Gynecologists cautions that the predictive value of this assessment is of uncertain significance because there are no therapies proven to prevent preterm birth.

The underlying cause of both post-term delivery and preterm delivery appears to be abnormal cervical remodeling (delayed in the first case, premature or accelerated in the second). Cervical remodeling occurs normally during pregnancy and results in a softening of cervical tissue before cervical shortening. The ability to accurately assess and study cervical remodeling (in an effort to understand normal versus abnormal changes) could provide improved prediction of preterm delivery, guide development of innovative therapeutic strategies, and permit treatment monitoring of those pregnancies, as well as predict which patients will have successful inductions of labor.

SUMMARY OF THE INVENTION

The present invention provides a method of directly and objectively measuring changes (collagen organization and softening) in cervical microstructure using backscattered ultrasound. The relationship between backscatter and angle can reveal the shape of microstructural scatterers, for example collagen within the cervix, whose reorganization is believed to be fundamental to cervical remodeling. This ultrasonic measurement of microstructure may be combined with an ultrasonic elasticity measurement (of softening) to produce a diagnostic tool for preterm delivery as well as for prediction of successful induction of labor.

Specifically then, the present invention provides a method of assessing cervical remodeling in pregnancy by applying an ultrasonic beam to the tissue of the cervical canal at a plurality of angles with respect to an axis of the cervix. Received echo signals are used to determine backscatter of the ultrasonic beam at the angles and processed to determine a relationship between angle and backscatter indicative of cervical remodeling. A measurement based on this relationship is output to an operator.

It is thus a feature of one embodiment of the present invention to assess cervical remodeling by measurement of small structures within cervical tissue.

The process of deducing the relationship between angle and backscatter may compensate for system-based, angle-related sensitivity of the ultrasound machine.

It is thus a feature of at least one embodiment of the invention to boost the sensitivity of the measurement by compensating for instrument-based backscatter variations.

The determination of the relationship between backscatter and angle may compare backscatter power over a range of frequencies at different angles.

It is thus a feature of at least one embodiment of the invention to provide a more robust measurement by evaluating multiple ultrasonic frequencies.

The determination of the relationship between backscatter and angle may combine backscattered data taken at symmetrical positive and negative angles about a normal to the cervical wall.

It is thus a feature of at least one embodiment of the invention to accentuate backscatter caused by microstructure such as should be symmetrical.

The plurality of angles may be within a plane containing the axis of the cervix and centered on a perpendicular to that axis and/or may be within a plane normal to the axis of the cervix and centered on a perpendicular to that axis.

It is thus a feature of at least one embodiment of the invention to permit multiple measurements of tissue of different microstructure orientations hypothesized to exist in the cervical wall.

An embodiment of the invention may include the step of measuring elasticity of the cervical tissue so that the output measurement may be a combination of elasticity and the relationship between backscatter and angle.

It is thus a feature of at least one embodiment of the invention to better differentiate between backscatter caused by tissue scatterer size and backscatter caused by cross-linking.

The elasticity may be obtained through acoustic radiation force impulse (ARFI) measurement.

It is thus a feature of at least one embodiment of the invention to provide a simple method of elasticity measurement that does not require compressive movement of the transducer or an independent compression probe, permitting use of an ultrasonic transducer within the cervical canal.

The ultrasonic transducer may have a diameter substantially less than 5 mm.

It is thus a feature of at least one embodiment of the invention to provide a probe that may be easily inserted into the cervix without substantially dilating the tissue to be measured.

The measurement may provide an indication of a likelihood of preterm delivery or an indication of likely due date.

It is thus a feature of at least one embodiment of the invention to provide simple metrics to a physician related to important information about a pregnancy.

These particular objects and advantages may apply to only some embodiments falling within the claims, and thus do not define the scope of the invention.

DETAILED DESCRIPTION OF THE PREFERRED EMBODIMENT

Figure 1:
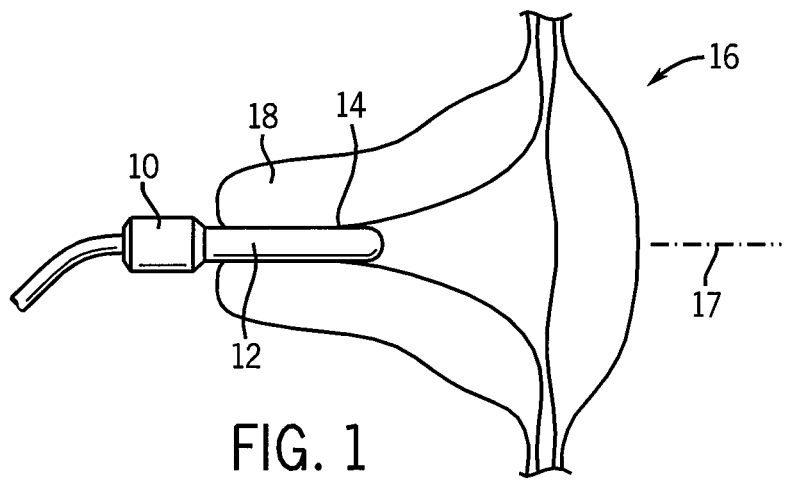
FIG. 1 is a simplified cross-sectional view of the uterus showing the cervical canal and an ultrasonic probe suitable for use with the present invention positioned within the cervical canal.

Referring now to FIG. 1, the present invention provides an ultrasound probe 10 having a generally cylindrical body 12 that may fit within the cervical canal 14 of the uterus 16 to extend along the uterine and cervical axis 17 and to be surrounded by cervical tissue 18. In a preferred embodiment, the cylindrical body 12 has an outside diameter substantially less than 5 mm so as to fit within the cervical canal without substantial dilation of the cervical tissue 18.

Figure 2:
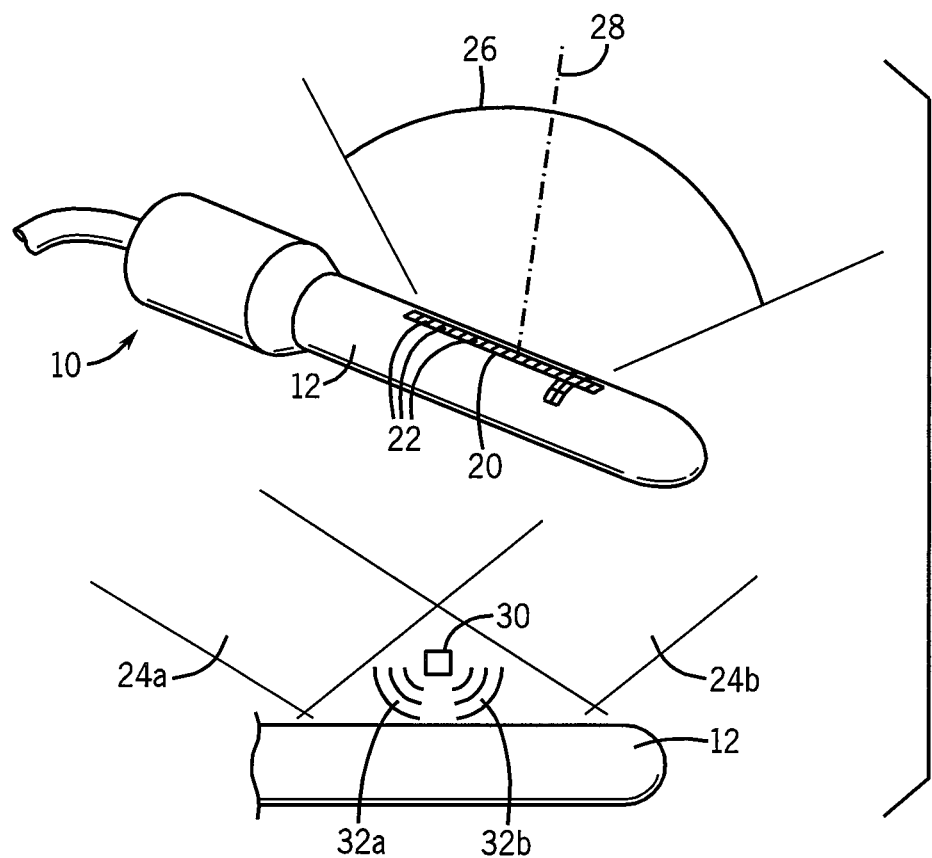
FIG. 2 is a perspective and side elevational view of the probe of FIG. 1 showing axial transducers for steering an ultrasonic beam at a range of axial angles within the cervix.

Referring now to FIG. 2, the outer surface of the cylindrical body 12 provides an axial transducer array 20 extending along the cylindrical body 12 and generally aligned with the axis 17 when the ultrasound probe 10 is within the cervical canal 14. The axial transducer array 20 has a plurality of independently operating transducer elements 22 that may provide for beam steering of a type known in the art. In particular, an ultrasonic beam 24 may be generated and steered over a range of axial angles 26 lying generally within a plane containing the axis 17 and symmetric about a center axis 28 perpendicular to axis 17. In the preferred embodiment, a range of ±20° is obtained. A beam 24a at one angular extreme and 24b at the other angle extreme can alternatively illuminate a voxel 30 of the cervical tissue 18 so that backscatter 32a or 32b at these two angular extremes and a range of angles in between may be collected by the same axial transducer array 20.

Figure 3:
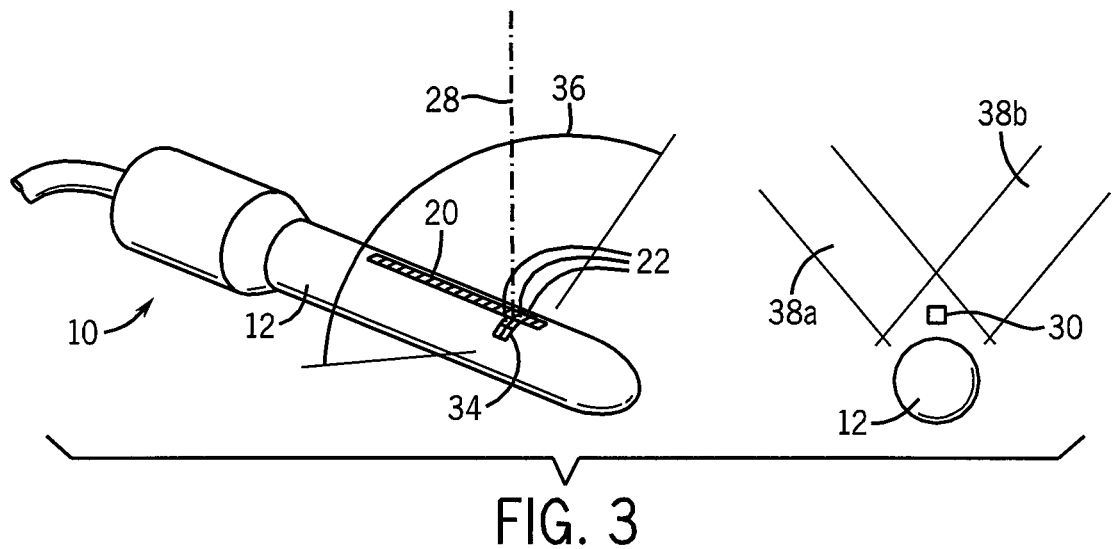
FIG. 3 is a figure similar to that of FIG. 2 providing a perspective and end elevational view of the probe of FIG. 1 showing circumferential transducers for steering an ultrasonic beam at a range of circumferential angles.

Referring to FIG. 3, a circumferential transducer array 34 may optionally be provided crossing the axial transducer array 20 at right angles and arranged around the circumference of the cylindrical body 12 to allow for beam steering of ultrasonic beam 38 within a range of angles 36 in a plane normal to the axis 17 and symmetric about the center axis 28. In this way, the voxel 30 may also be illuminated by beams 38a and 38b over the range of angles 36 and backscatter detected at the cylindrical body 12.

In one embodiment, the transducer array may provide for 7.5 MHz operation with 64 array elements at 100 µm pitch. It will be understood that a two dimensional transducer array having multiple perpendicular rows and columns can be used instead of the cruciform array described above to provide measurements of the ranges of both angles 26 and 36.

Figure 4:
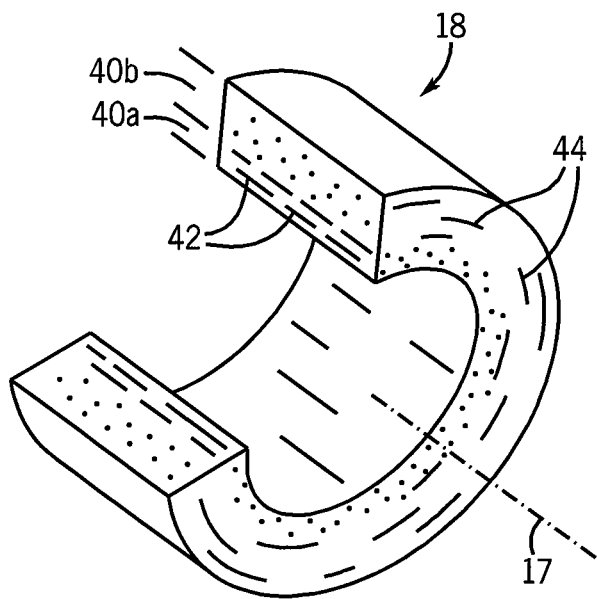
FIG. 4 is an exaggerated fragmentary cross-sectional view of the cervical tissue showing a hypothesized organization of collagen in the cervical tissue early in pregnancy.

Referring now to FIG. 4, while the inventors do not wish to be bound by a particular theory, it is believed that the cervical tissue 18 is comprised of at least two layers of collagen-based tissue including an inner layer 40a and an outer layer 40b. The inner layer 40a may contain collagen fibers 42 arranged parallel to the axis 17 that may be measured by the beams 24 produced by the axial transducer array 20, whereas the outer layer 40b may contain collagen fibers 44 arranged circumferentially about axis 17 to be measured by the beams 38 produced by the circumferential transducer array 34.

Figure 5:
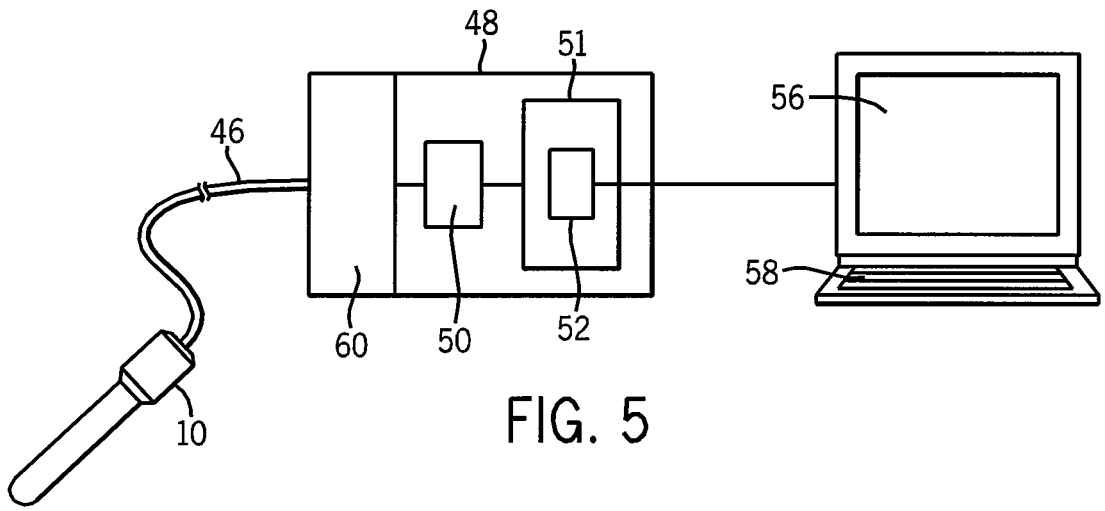
FIG. 5 is a block diagram of an ultrasound machine suitable for use with the probe of FIGS. 1-3 including a processor executing a stored program to process data used in the present invention.

Referring now to FIG. 5, the ultrasound probe 10 may communicate via a flexible cable 46 with an ultrasound machine 48 of the type generally known in the art including, for example, a digital signal processor 60 receiving ultrasonic data and generating ultrasonic output signals, in turn communicating with a standard computer processor 50 executing a program 52 contained in memory 51 to implement the present invention. Generally, the ultrasound machine 48 may also communicate with the display terminal 56 for the outputting of data and a user data entry device 58 such as a keyboard or the like to control operation of the ultrasound machine and to input data according to techniques well known in the art.

Generally phased ultrasonic signals will be created by a digital signal processor 60 under instructions from the processor 50 and transmitted along cable 46 to the transducer arrays of the ultrasound probe 10 to create ultrasonic beams at desired angles and to measure backscatter therefrom. The backscatter signals will be received by ultrasound probe 10 and transmitted through cable 46 to the digital signal processor 60 for analysis by the program 52, the results of which may be displayed on the terminal 56 as will be described.

Figure 6:
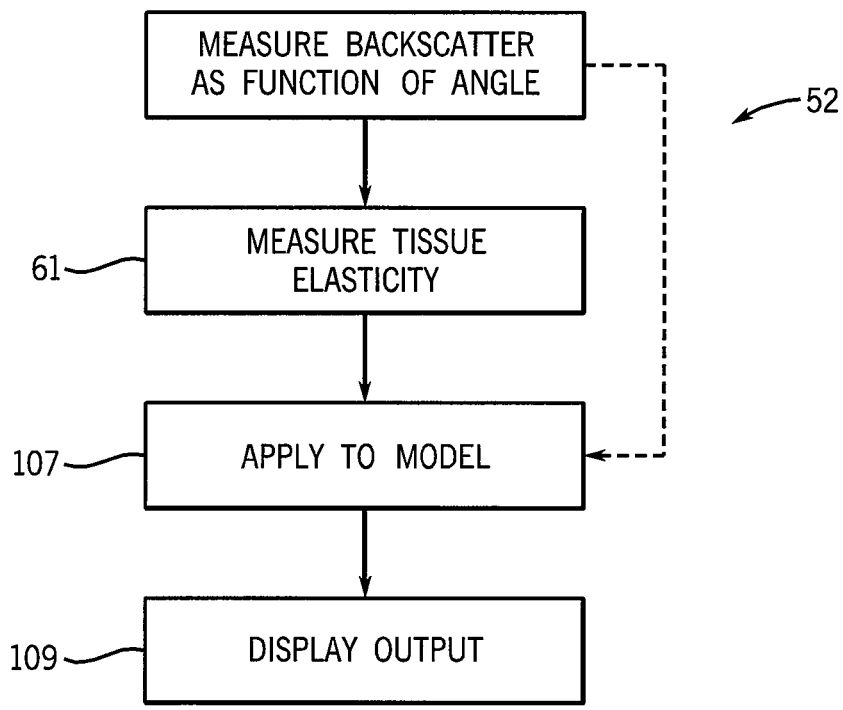
FIG. 6 is a flowchart of the program used in the processor of FIG. 5.

Referring now to FIG. 6, at a first step of the program 52 indicated by process block 62, ultrasonic beams are generated either axially or circumferentially or both, at a range of frequencies, and backscatter acoustic power from those beams is measured by the ultrasound probe 10 for analysis.

Figure 7:
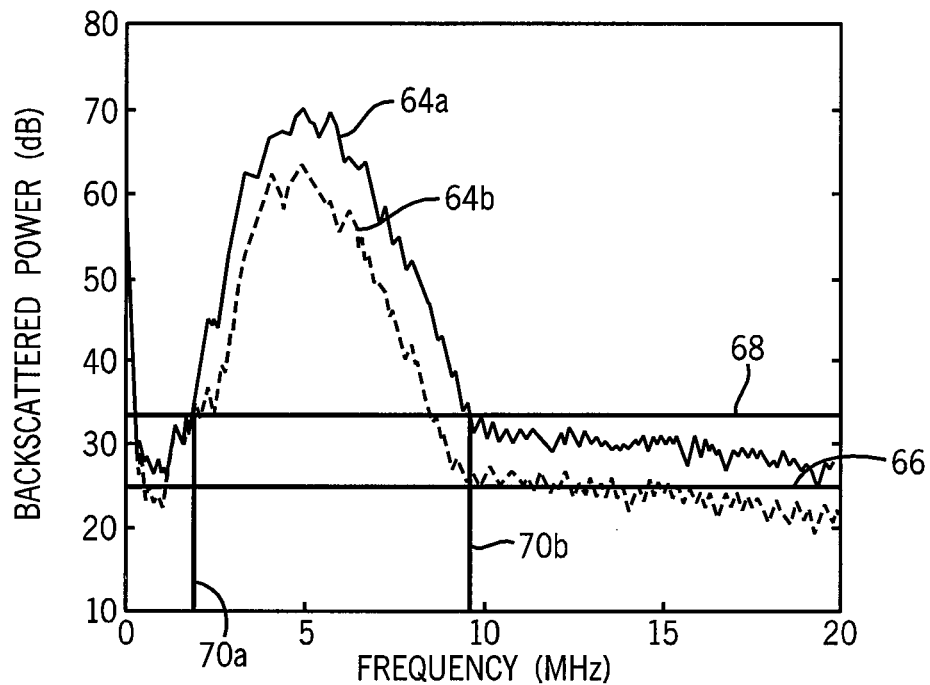
FIG. 7 is a plot of backscatter power spectra at different beam angles showing a decrease in backscatter power at increased angles as a function of frequency.

Referring now to FIG. 7, backscatter information obtained over a range of frequencies at a range of angles provides multiple power spectra 64a and 64b. In this figure, power spectrum 64a is taken normal to the cervical wall along the center axis 28 exhibiting the highest degree of backscatter and power spectrum 64b is a combination (averaging) of the power spectra obtained at the extreme angles of the beam angulation (i.e. ±20°). Because the tissue structure effects intended to be measured will be symmetric about center axis 28, this averaging process provides for improved signal-to-noise ratio in the measurement while rejecting asymmetrical effects. Multiple additional power spectra may optionally be obtained at different angles.

In a preferred embodiment, the axial transducer array 20 is used to obtain measurements of backscatter at shallow voxel depths corresponding to layer 40a of FIG. 4, and circumferential transducer array 34 is used to obtain power spectra at deeper voxel depths corresponding to layer 40b of the tissue 18.

In a simple embodiment, backscatter at each depth may be characterized by these two power spectra 64a and 64b by establishing a noise floor 66, representing the lowest signal strength of the power spectrum for either of the spectra 64a or 64b and determining a 10 db limit 68 above this noise floor 66 used to define upper and lower frequency limits 70a and 70b of the power spectra 64a and 64b. Between these limits 70a and 70b, the area under each of the spectra 64a and 64b is integrated (for example, from frequencies from 3 to 9 MHz). The resultant backscatter power measurement at the extreme angles (64b) is compared to the backscattered power 64a at zero-degree steering angle (perpendicular to the cervical axis 17).

This measured-backscattered power value is then compared to a machine-backscattered power value (not shown) resulting from machine specific features, for example, the effective reduction in ultrasound aperture with angle caused by geometrical considerations and a decrease in the sensitivity of the axial transducer array 20 and circumferential transducer array 34 with angle, both of which cause an machine-dependent apparent loss in backscatter power. The machine specific backscattered power value may be determined by the use of a phantom containing spherical isotropic scatterers. This machine-backscattered power value may be computed for each measurement from a stored power spectrum (not shown) using the same integration limits 70a and 70b described above. The measured-backscattered power value is corrected by the machine-backscattered power value to reveal the excess backscattered power loss caused by structure of the cervical tissue 18. This latter excess-backscattered power loss value from each of the axial transducer array 20 and circumferential transducer array 34 may be weighted and combined or displayed individually to the user through the graphic terminal 56 or may be further processed as will be described further below.

Figure 8:
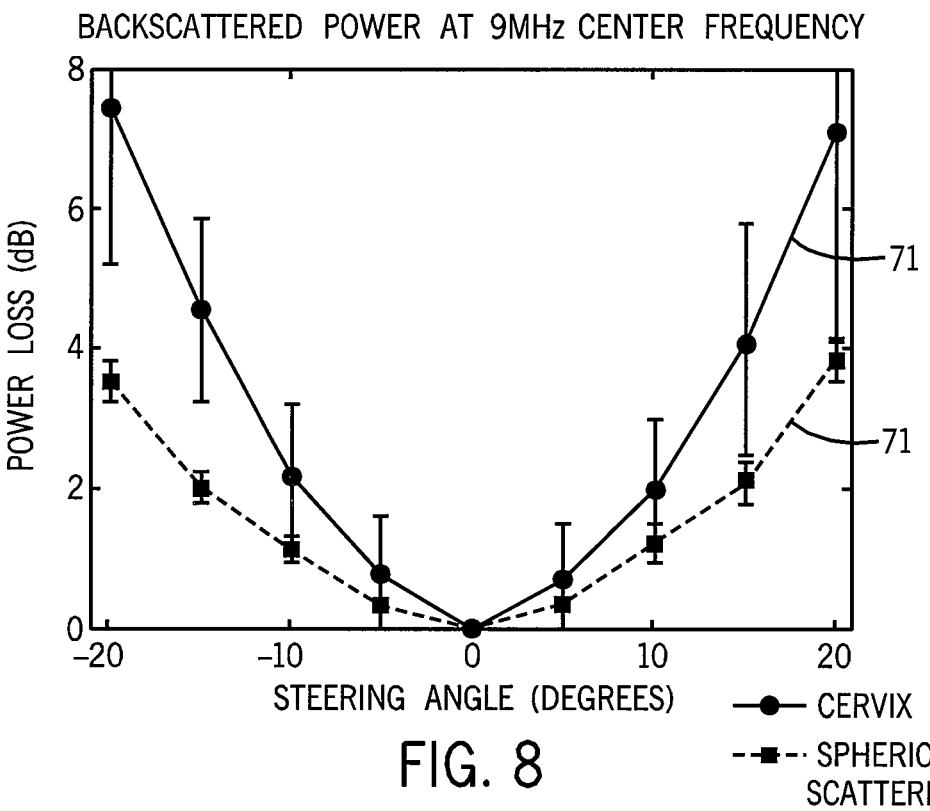
FIG. 8 is a plot of backscatter as a function of angle for center frequencies of 9 MHz for cervical tissue and for a phantom with spherical scatterers.

Referring now to FIG. 8, an alternative measurement of backscatter computes received backscatter power curves 71 as a function of one or more frequencies at multiple angular measurements 72 for both the phantom described above and the cervical tissue 18. A difference in slope of these curves 71 provides the excess-backscattered power loss value that may be displayed to the user as above.

Referring again to FIG. 7, an alternative measurement parameterizing backscatter, such as the backscatter coefficient, effective scatterer size, integrated backscatter, mean scatterer spacing or number of scatterers per unit volume could be derived from these angle-dependent power spectra and used to describe the cervical tissue in greater detail.

Alternatively, in any of these cases, the angle related excess-backscattered power loss, or related parameter, as quantified (in one or more dimensions) may be applied to an empirically-derived model that may include additional input parameters entered by the user, for example, conception date, cervical length, age of the patient and other data. The model then provides a statistically founded output related to fundamental information desired by the physician, for example risk of preterm delivery, or state of the cervix with respect to a state for successful delivery as will be described below.

In a preferred embodiment the excess-backscattered power loss is combined with elasticity data for the same tissue. The elasticity data augments the backscatter data to better distinguish among microstructure with similar backscattering but different elasticities. While the applicant does not wish to be bound to a particular theory, it is believed that backscatter power loss is increased when the beam encounters anisotropic tissue such as exists in the unripened cervix in comparison to when the beam encounters isotropic tissue in the ripened cervix. This unripened tissue appears to be made up of organized, cylindrical microstructures. At normal incidences (that is, when the cylinder axes of the microstructures are perpendicular to the propagation axis of the ultrasonic wave) a cylinder that is small compared to the acoustic wavelength (as is expected to be the case with collagen structures in the cervix) creates a backscattering that can be explained primarily in terms of resonances related to elastic circumferential waves. However, a wave that encounters a cylinder at a non-normal angle to its axis (either positive or negative angle) excites both longitudinal and circumferential modes of vibration increasing power loss. The extent of the power loss, therefore, can reveal the degree of organization of the tissue.

Backscatter, however, will be similar for long cylindrical fibers that are cross-linked and short cylindrical fibers with no cross-linking. Accordingly, elasticity can be used to resolve these two cases with the longer fibers that produce generally a stiffer and less elastic tissue distinguished by their elasticity from the shorter fibers.

Figure 9:
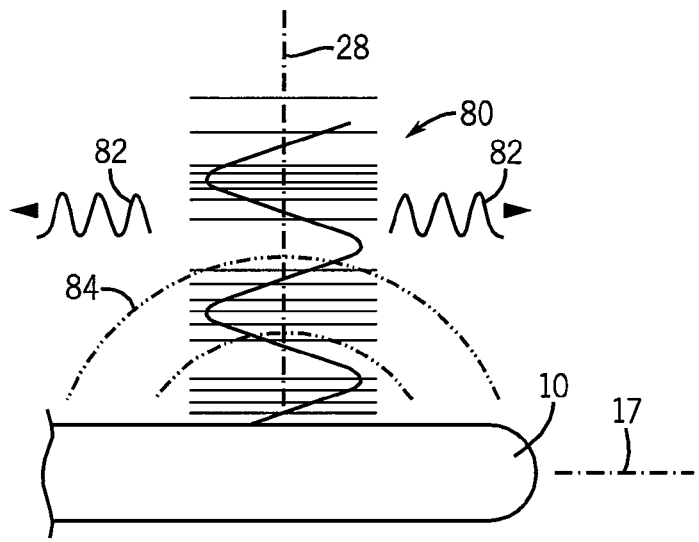
FIG. 9 is a side elevational view of the probe of FIG. 1 in the cervix showing the excitation of shear waves from a "pushing pulse" emitted by the probe in quantitative acoustic radiation force impulse measurements.

Referring now to FIG. 9 and as shown by process block 61 of FIG. 6, the ultrasound probe 10 may be used to measure not only the backscatter as described above, but also the elasticity of the tissue 18 by using the technique of quantitative acoustic radiation force impulse (qARFI). In this technique, a focused compression "push wave" 80 is generated generally along center axis 28 which produces incidental shear waves 82 passing through the tissue 18 generally parallel to the axis 17. B-mode imaging pulses 84 may be used to detect the tissue displacement caused by the shear waves 82 and track a crest of those waves to determine shear wave velocity such as is proportional to Young's modulus, a measure of elasticity. Tools for qARFI and are available from Siemens under the trade name ACUSON S2000 (Virtual Touch Tissue Quantification).

Figure 10:
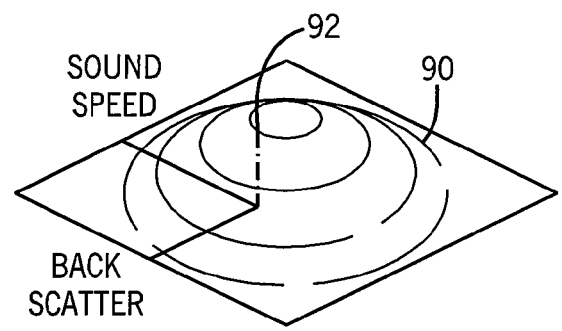
FIG. 10 is a simplified model relating backscatter loss and elasticity to empirically derived preterm risk boundaries.
Figure 11:
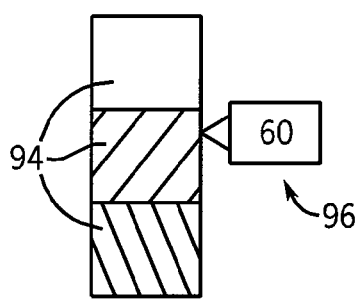
FIG. 11 is an example output displayed for the ultrasound machine of FIG. 5 depicting a risk of preterm delivery in simplified fashion.

Referring to FIG. 10, a model 90 may be generated (in this case depicted as a 3-dimensional surface) that takes backscatter power loss and shear wave sound speed as inputs to provide an output point 92 on a model surface empirically linked to risk of preterm delivery. As indicated by the FIG. 11, this output point 92 may be mapped to a simple scale 94 depicting risk of preterm delivery relative to broad categories, for example high-risk, medium risk, and low risk, and/or a numeric output 96 may be provided providing the same information, for example, as a percentage. The model may incorporate additional input dimensions as described above, such as gender, conception date, and the like, such multidimensional models providing a multidimensional surface not readily depicted.

Figure 12:
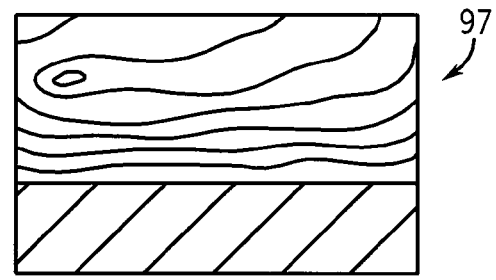
FIG. 12 is a graphical display of a backscatter power image for investigational study.

Referring to FIG. 12, elasticity data and backscatter data may also be displayed as an image 97 in the manner of a conventional B-mode image or superimposed on a B-mode image to characterize different portions of the cervical tissue in the image. In this way, the phenomenon of graduated ripening of the cervix from the proximal to distal portions may be studied.

Figure 13:
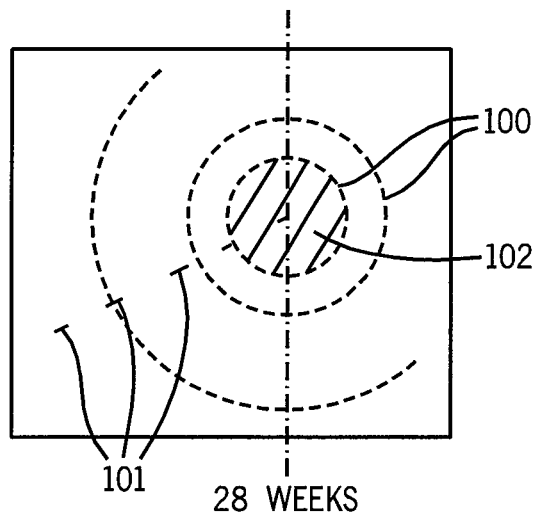
FIG. 13 is a graphical display representing a model of backscatter measurements during a normal pregnancy superimposed on measurements from a particular patient used for predicting due date or making decisions about delivery.
Figure 14:
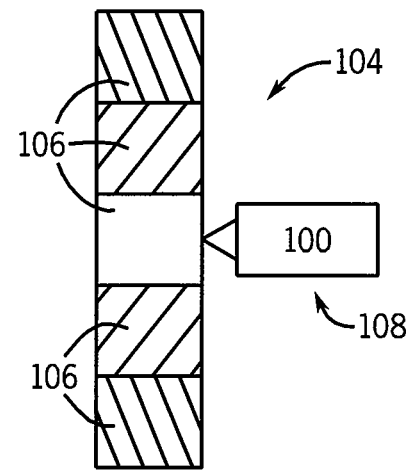
FIG. 14 is a figure similar to that of FIG. 11 showing a simplified display indicating concurrence between a given pregnancy and a statistically normal pregnancy.

Referring now to FIG. 13 and as shown by process block 107 of FIG. 6, it will be understood that the measured data of backscatter and/or shear wave sound speed may also be used to evaluate the course of pregnancy, for example, by the generation of boundaries 100 indicating the state 102 of remodeling of the cervix, for example, at the time of a standard vaginal delivery in a sampled population together with data from an individual patient, assisting the physician in assessing a due date and or appropriate time for induced labor for delivery. Again, as shown in FIG. 14 and process block 109 of FIG. 6, the data of the model of FIG. 13 may be extracted to a simple display 104 having zones 106 showing degrees of remodeling of the cervix for delivery and providing a quantitative output 108 for the physician.

Figure 15:
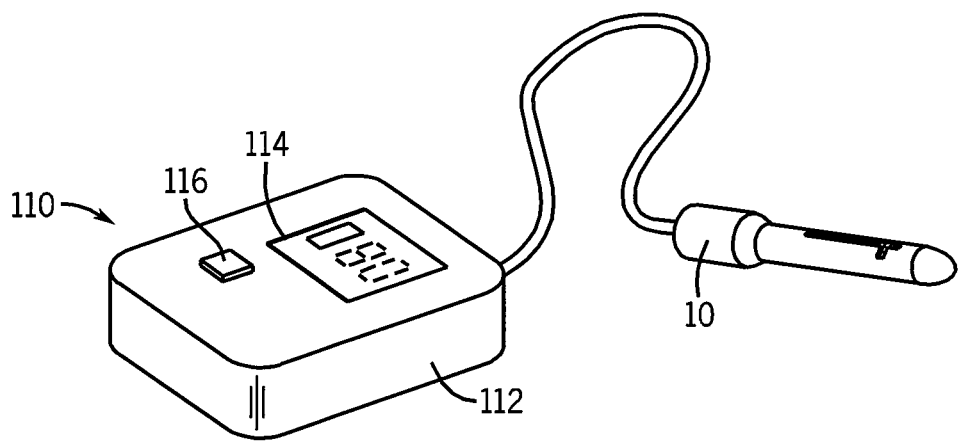
FIG. 15 is a perspective representation of a handheld device for implementing the present invention.

Referring to FIG. 15, although the present invention may be incorporated into a standard imaging ultrasound machine providing B-mode imaging capabilities, the present invention may also be provided in a portable stand-alone instrument 110 in which the ultrasound probe 10 may connect to a handheld unit 112 providing a simple graphic display 114 and as little as a single activation button 116, and preprogrammed to make the measurements of the present invention.

It is specifically intended that the present invention not be limited to the embodiments and illustrations contained herein, but include modified forms of those embodiments including portions of the embodiments and combinations of elements of different embodiments as come within the scope of the following claims. For example, the invention does not require a cervical probe but conceivably could be done transabdominally.

We claim:

1. A method of assessing cervical remodeling in pregnancy comprising using an ultrasound machine operating according to a stored program executable on an electronic computer according to the program stored in a non-transitory, tangible computer readable storage medium to:
   (a) apply an ultrasound beam to a volume element of tissue of a cervical canal to provide overlapping measurements of tissue of the volume element at multiple different angles with respect to a line perpendicular to an axis of the cervix;
   (b) receive echo signals with the ultrasound machine at each of the different angles to obtain for each of the different angles, quantitative backscatter measurements from the tissue of the volume element wherein the backscatter quantitative measurements are measurements of acoustic power,
   (c) process the backscatter measurements to compare at least a first backscatter measurement of the volume element made at a first angle of the multiple different angles, to at least a second backscatter measurement of the same tissue of the volume element made at a second angle of the multiple different angles, the second backscatter measurement made contemporaneously with the first backscatter measurement, to determine a value indicating an amount of change in backscatter acoustic power between the measurements of the same tissue at the different angles for the volume element; and
   (d) output a diagnostic indication to an operator indicating cervical remodeling based on the amount of change in backscatter acoustic power between the measurements of the same tissue at the different angles for the volume element.

2. The method of claim 1 wherein the determining of the change compensates the backscatter measurements for system-based angle related sensitivity of the ultrasound machine.

3. The method of claim 1 wherein the backscatter measurement compares integrated power over a range of frequencies at different angles.

4. The method of claim 1 wherein the determining of the change combines backscattered data taken at symmetrical positive and negative angles about a normal to the cervical wall.

5. The method of claim 1 wherein backscatter measurement is selected from the group consisting of backscatter power loss, effective scatterer size, integrated backscatter, mean scatterer spacing, and number of scatterers per unit volume.

6. The method of claim 1 wherein the multiple angles are within a plane containing the axis of the cervix and centered on a perpendicular to that axis.

7. The method of claim 1 wherein the multiple angles are within a plane normal to the axis of the cervix and centered on a perpendicular to that axis.

8. The method of claim 1 further including the step of measuring elasticity of the cervical tissue and where the diagnostic indication is a combination of elasticity and the determined change.

9. The method of claim 8 wherein the elasticity is obtained through acoustic radiation force impulse measurement.

10. The method of claim 1 wherein the ultrasonic beam is directed from an ultrasonic transducer within the cervical canal.

11. The method of claim 10 wherein the ultrasonic transducer is sized whereby the cervical canal is dilated to a diameter substantially less than 5 mm in the step of directing the ultrasonic beam from the ultrasonic transducer within the cervical canal.

12. The method of claim 1 wherein the diagnostic indication is an indication of a likelihood of preterm delivery.

13. The method of claim 1 wherein the diagnostic indication is an indication of likelihood of successful induction of labor at term.

14. An ultrasound machine comprising: an ultrasound transducer for transmitting ultrasonic waves and receiving echoes; an electronic display; a memory storing a program; an electronic signal processor communicating with the ultrasound transducer and the display and the memory and executing a stored program executable on an electronic computer according to the program stored in a non-transitory, tangible computer readable storage medium to:
   (a) apply an ultrasonic beam to a volume element of tissue of a cervical canal to provide overlapping measurements of tissue of the volume element at multiple different angles with respect to a line perpendicular to an axis of the cervix wherein the ultrasonic beams at different angles intersect at the volume element to define an area of interest of the tissue;
   (b) receive echo signals with the ultrasound machine at each of the different angles to obtain for each of the different angles, quantitative backscatter measurements from the area of interest wherein the backscatter quantitative measurements are measurements of acoustic power;
   (c) process the backscatter measurements to compare at least a first backscatter measurement of the volume element made at a first angle of the multiple different angles, to at least a second backscatter measurement of the same tissue of the volume element made at a second angle of the multiple different angles, the second backscatter measurement made contemporaneously with the first backscatter measurement, to determine a value indicating an amount of change in backscatter acoustic power between the measurements of the same tissue at the different angles for the volume element; and (d) output a diagnostic indication indicating cervical remodeling based on the amount of change in backscatter acoustic power between the measurements of the same area of interest at the different angles for the volume element.

15. The ultrasound machine of claim 14 wherein the stored program further executes so that the determination of the change compensates the backscatter measurement with a baseline backscatter of an isotropic phantom.

16. The ultrasound machine of claim 14 wherein the stored program further executes so that backscatter measurement is selected from the group consisting of backscatter power loss, effective scatterer size, integrated backscatter, mean scatterer spacing, and number of scatterers per unit volume.

17. The ultrasound machine of claim 14 wherein the stored program further executes to operate the ultrasonic probe to provide an ultrasonic beam at a range of positive and negative angles about a normal to the cervical wall.

18. The ultrasound machine of claim 14 wherein the ultrasonic transducer is substantially cylindrical to fit within the cervical canal and includes at least two arrays of transducers, a first array extending along an axis of the cylinder and a second array extending perpendicularly to the first array about a circumference of the cylinder.

19. The ultrasound machine of claim 14 further executing the stored program to:

(e) direct a beam of ultrasound through the tissue of the cervical canal to promote shear waves perpendicular to the beam;

(f) measure a velocity of the shear waves by ultrasonic imaging to deduce tissue elasticity;

wherein the diagnostic indication is based on the relationship and on the tissue elasticity.

* * * * *